United States Patent
Pandya et al.

(10) Patent No.: US 11,464,545 B1
(45) Date of Patent: Oct. 11, 2022

(54) ANTI-SPLAY BONE ANCHOR

(71) Applicant: Indius Medical Technologies Private Limited, Maharashtra (IN)

(72) Inventors: Meet Pandya, Gujarat (IN); Piyali Gokhale, Maharashtra (IN); Aditya Ingalhalikar, Maharashtra (IN); Sagar Sathaye, Maharashtra (IN)

(73) Assignee: INDIUS MEDICAL TECHNOLOGIES PRIVATE LIMITED, Maharashtra (IN)

( * ) Notice: Subject to any disclaimer, the term of this patent is extended or adjusted under 35 U.S.C. 154(b) by 0 days.

(21) Appl. No.: 17/484,277

(22) Filed: Sep. 24, 2021

(30) Foreign Application Priority Data

Jul. 2, 2021 (IN) .............. 202121029739

(51) Int. Cl.
*A61B 17/70* (2006.01)
*A61B 17/86* (2006.01)

(52) U.S. Cl.
CPC ...... *A61B 17/7032* (2013.01); *A61B 17/8685* (2013.01)

(58) Field of Classification Search
CPC ............ A61B 17/7032; A61B 17/8685
USPC ................... 606/270, 272, 273, 308
See application file for complete search history.

(56) References Cited

U.S. PATENT DOCUMENTS

| | | | |
|---|---|---|---|
| 6,565,565 B1 | 5/2003 | Yuan et al. | |
| 7,125,426 B2 | 10/2006 | Moumene et al. | |
| 7,811,310 B2 | 10/2010 | Baker et al. | |
| 8,092,494 B2* | 1/2012 | Butler | A61B 17/7032 606/246 |
| 8,162,989 B2 | 4/2012 | Khalili | |
| 8,475,495 B2 | 7/2013 | Iott et al. | |
| 8,740,946 B2* | 6/2014 | Peterson | A61B 17/7037 606/264 |
| 8,790,374 B2 | 7/2014 | Iott et al. | |
| 9,138,262 B2 | 9/2015 | Iott et al. | |
| 9,439,682 B2 | 9/2016 | Iott et al. | |
| 9,439,700 B2 | 9/2016 | Peterson et al. | |
| 9,750,542 B2 | 9/2017 | Iott et al. | |
| 9,795,415 B2 | 10/2017 | Bono et al. | |
| 9,949,766 B2 | 4/2018 | Iott et al. | |
| 9,980,754 B2 | 5/2018 | Harper et al. | |

(Continued)

FOREIGN PATENT DOCUMENTS

| | | |
|---|---|---|
| AU | 2002301198 B2 | 8/2007 |
| CN | 101966096 B | 3/2014 |

*Primary Examiner* — Eduardo C Robert
*Assistant Examiner* — David C Comstock
(74) *Attorney, Agent, or Firm* — Foley & Lardner LLP

(57) ABSTRACT

An anti-splay bone anchor is provided. The anti-splay bone anchor comprises a screw shank, a screw head and a locking cap member as the primary components. The screw head comprises a first opposing member having a first profile and a second opposing member having a second profile; a through hole for receiving the screw shank there-through. The locking cap member comprises a body, a through hole, a set screw and a first and a second tab. The through hole has threads on the inner surface which is adapted to threadably receive the set screw having threads on the outer surface. The first tab and the second tab, each extending radially outward from the locking cap member, have a third and a fourth profile which are complimentary to the first profile and the second profile, respectively.

6 Claims, 19 Drawing Sheets

(56) References Cited

U.S. PATENT DOCUMENTS

| | | |
|---|---|---|
| 10,299,834 B2 | 5/2019 | Iott et al. |
| 2002/0120272 A1* | 8/2002 | Yuan .................. A61B 17/7032 606/272 |
| 2003/0187434 A1* | 10/2003 | Lin .................... A61B 17/7034 606/272 |
| 2006/0079895 A1 | 4/2006 | McLeer |
| 2006/0161152 A1* | 7/2006 | Ensign ............... A61B 17/7032 606/279 |
| 2009/0030457 A1* | 1/2009 | Janowski ........... A61B 17/7037 606/301 |
| 2009/0062866 A1* | 3/2009 | Jackson ................ A61B 17/86 606/301 |
| 2013/0066380 A1* | 3/2013 | Haskins ............. A61B 17/8685 606/305 |
| 2019/0274738 A1* | 9/2019 | Heuer ................ A61B 17/7076 |
| 2021/0059723 A1* | 3/2021 | Biedermann ...... A61B 17/7035 |

\* cited by examiner

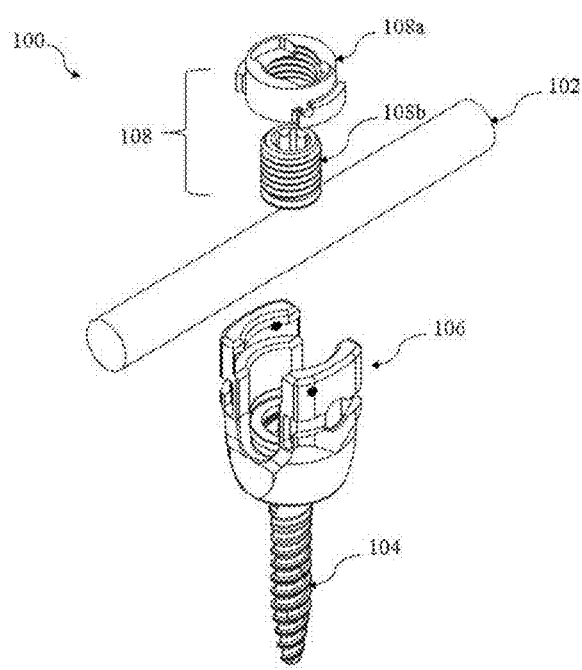 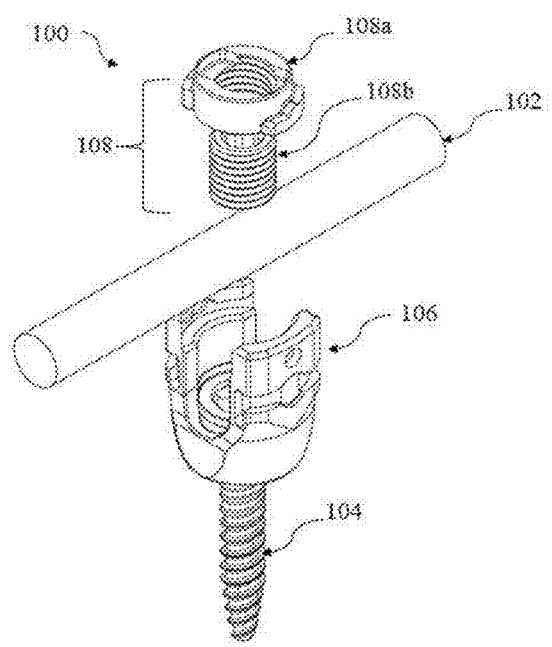
Figure 1aFigure 1b

ANTI-SPLAY BONE ANCHOR

The present application takes priority from the previously filed Indian Provisional application number 202121029739 titled "ANTI-SPLAY BONE ANCHOR" dated Jul. 2, 2021.

FIELD

The present disclosure relates to bone anchors. Particularly, the present disclosure relates to bone anchors for use in orthopedic surgeries.

BACKGROUND

Bone anchors such as pedicle screws are typically used in orthopedic surgeries to correct deformity and/or treat trauma. The pedicle screws are commonly used to affix rods and plates to the bony anatomy or to immobilize a part of the bony anatomy to assist fusion by holding the bony structures together. Pedicle screw systems typically have a locking cap assembly and a pedicle screw assembly as the main components, wherein the pedicle screw assembly is adapted to be affixed onto the bony anatomy and the locking cap assembly is adapted to receive and lock the rod or plate in place.

Currently available pedicle screw systems are associated with several drawbacks. One significant drawback is splay. Since the outer operative surface of the locking caps is threaded, it causes the screw head to splay, during engagement with the screw head. This makes the grip insecure leading to serious safety concerns. Furthermore, since the locking caps are threaded, engagement with the screw head takes a lot of time and also leads to cross threading, leading to thread breakage and ultimately loosening of the construct. Still further, since the locking is dependent solely on the force of friction, due to the natural jerks and twists of the body, there is a chance of the cap backing out of the engagement, which can be extremely risky.

The inventors of the present disclosure have envisaged an anti-splay bone anchor which addresses the afore-mentioned drawbacks.

OBJECTS

It is an object of the present disclosure to provide an anti-splay bone anchor.

It is another object of the present disclosure to provide an anti-splay bone anchor which is safe.

It is yet another object of the present disclosure to provide an anti-splay bone anchor which is economical.

It is still another object of the present disclosure to provide an anti-splay bone anchor which is simple in construction and has less number of components.

It is yet another object of the present disclosure to provide an anti-splay bone anchor which is easy to operate.

It is still another object of the present disclosure to provide an anti-splay bone anchor which can be anchored on the bone in a short period of time.

SUMMARY

The present disclosure provides an anti-splay bone anchor for attaching at least one rod member to a bone. The bone anchor comprises a screw shank, a screw head and a locking cap member as the primary components. The screw head comprises a first opposing member having a first profile and a second opposing member having a second profile and a through hole for receiving said screw shank there-through. The locking cap member comprises a body, a through hole, a set screw and a first and second tab. The through hole has threads on the inner surface which is adapted to threadably receive the set screw having threads on the outer surface. The through hole is also configured to abut and clamp said rod member to said screw head. The first tab and a second tab each extending radially outward from said locking cap member, have a third and a fourth profile which are complimentary to said first profile and said second profile, respectively.

In an operative configuration, after receipt of said rod member within the screw head, the locking cap member is received and rotated in the screw head through a predetermined angle, such that a clearance is maintained therebetween. After completing the rotation of the locking cap member, there is an interference between the first tab and the second tab with the first profile and the second profile, respectively; said interference being axial and designed to be overcome by rotating the locking cap member further until no rotation is possible. After receipt and tightening of the set screw in the through hole, the locking cap member is lifted up to facilitate complete engagement of the first and the second profile with the third and the fourth profile respectively; thereby causing the locking cap member to be positively locked in the axial direction.

BRIEF DESCRIPTION OF THE ACCOMPANYING DRAWINGS

The present disclosure is illustrated in the accompanying non-limiting drawings, throughout which like reference letters indicate corresponding parts in the various figures.

FIGS. 1a and 1b illustrate two embodiments of the bone anchor (100) of the present disclosure.

Figure 7A:
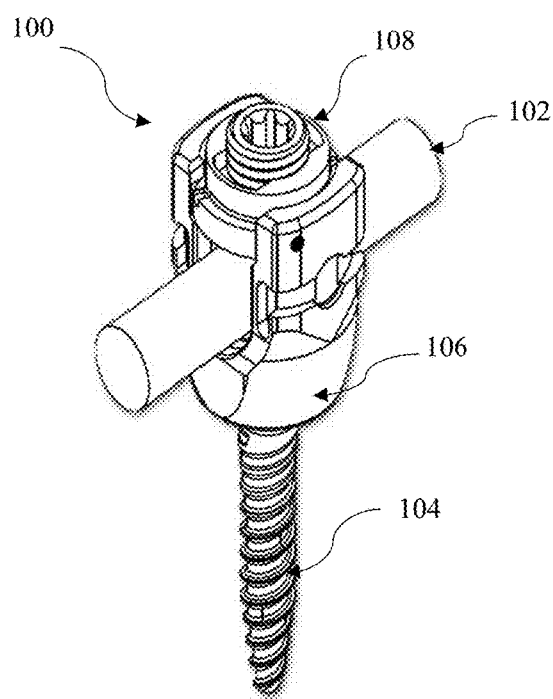
Figure 7B:
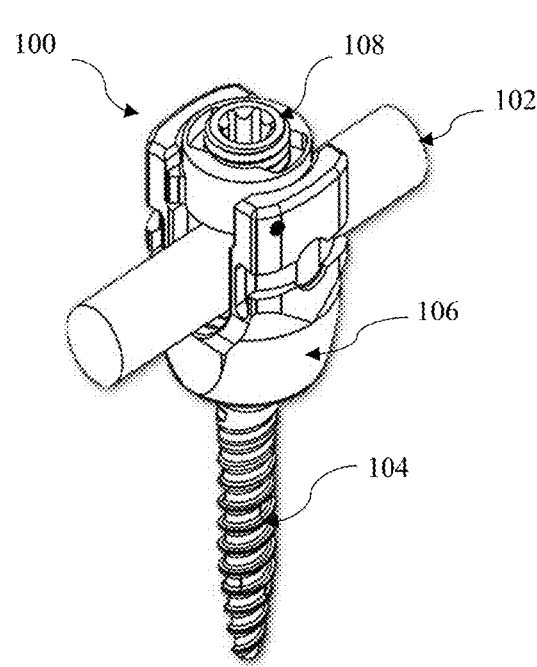
Figure 7C:
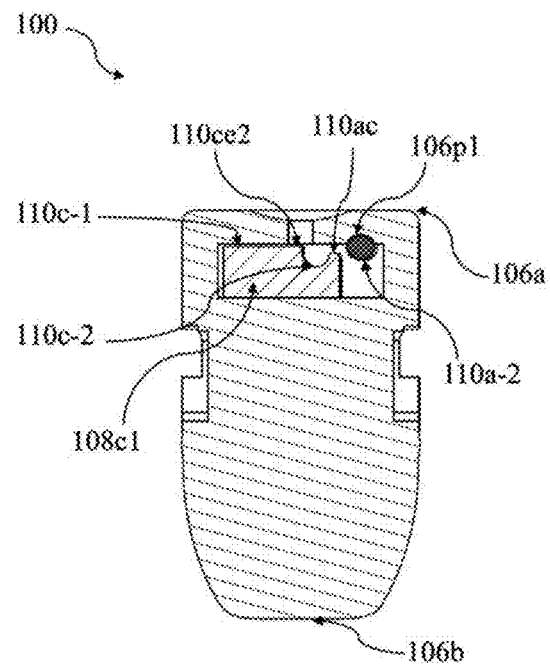
Figure 7E:
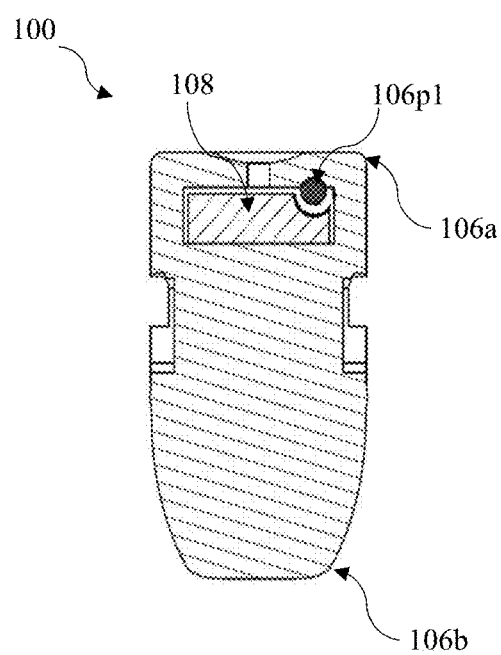
Figure 7F:
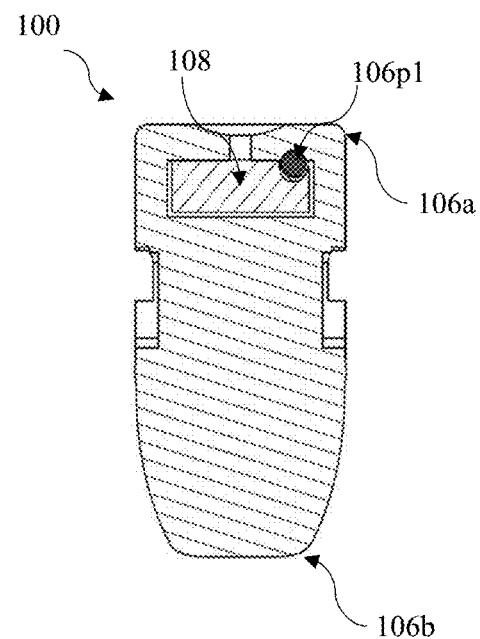
Figure 7D:
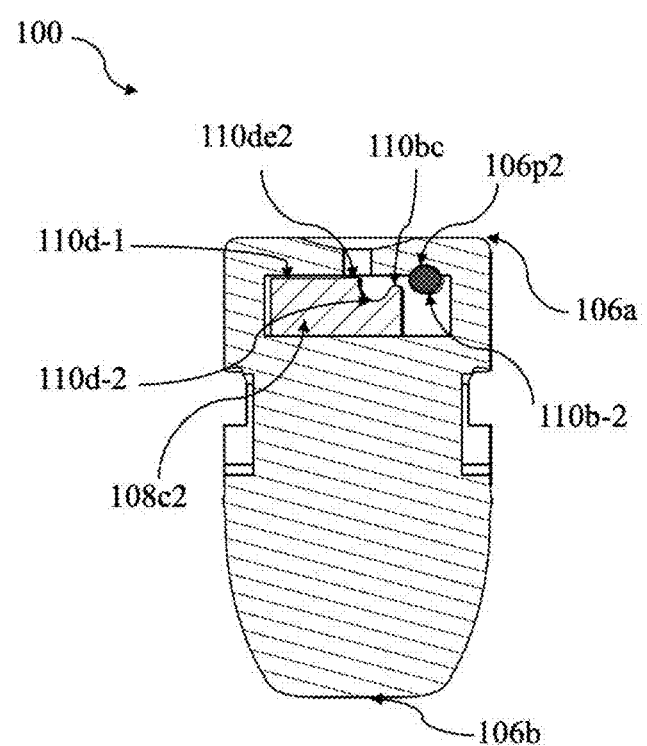

FIGS. 7a, 7b, 7c, 7e, and 7f represent the process of one embodiment of the bone anchor (100) being installed, with FIGS. 7a and 7b being the perspective views of the entire bone anchor (100) and FIGS. 7c, 7e, and 7f being the side views showing the engagement of the locking cap member (108) with the screw head (106). FIG. 7d illustrates the profiles of the locking cap member (108) and the screw head (106), correspondingly opposite, to those illustrated in FIG. 7c.

Figures 8A, 8B:
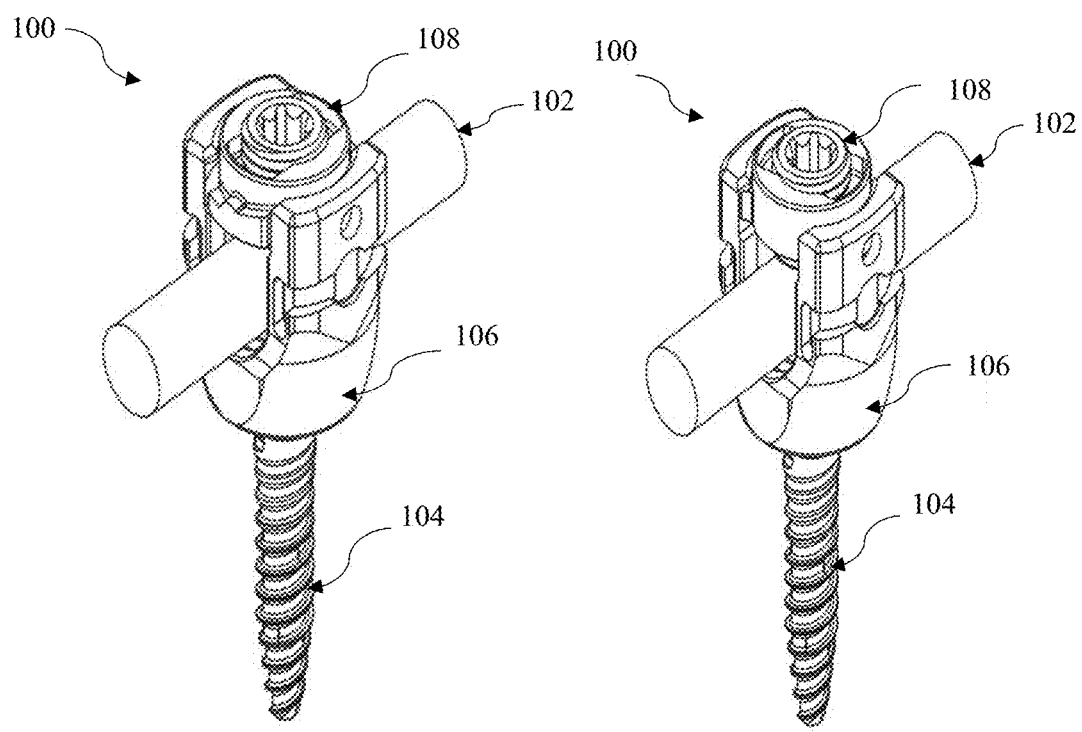
Figure 8C:
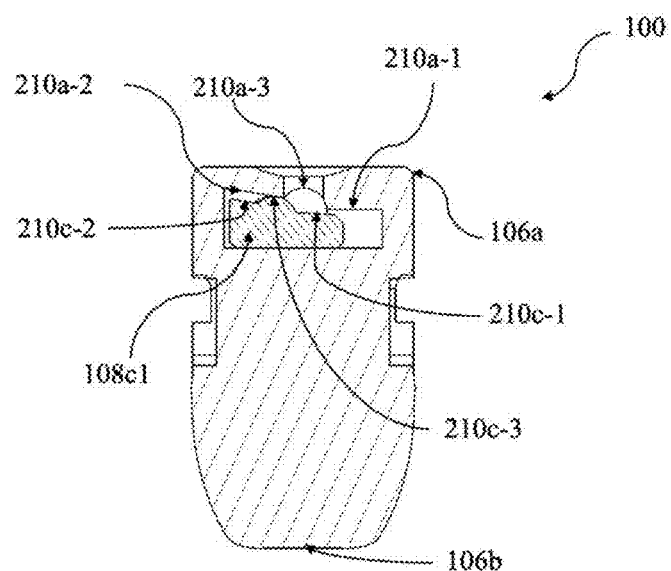
Figure 8E:
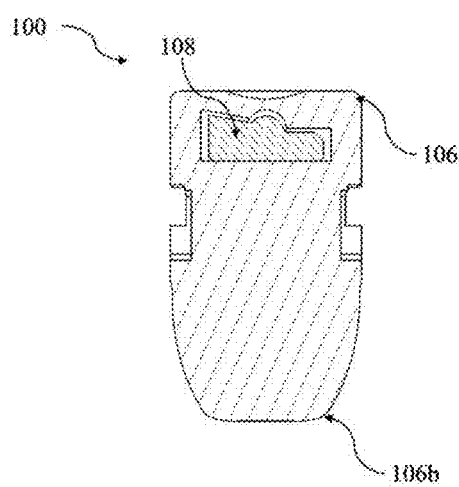
Figure 8F:
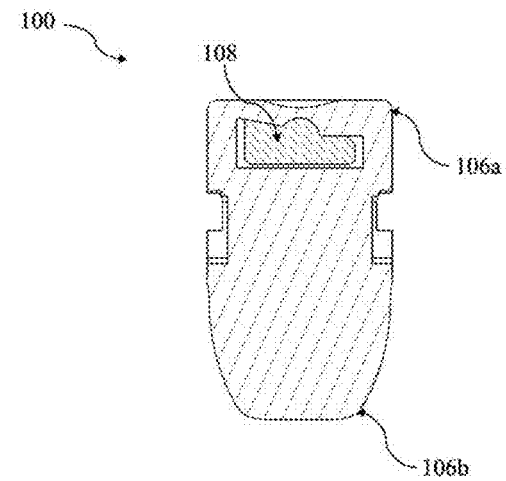
Figure 8D:
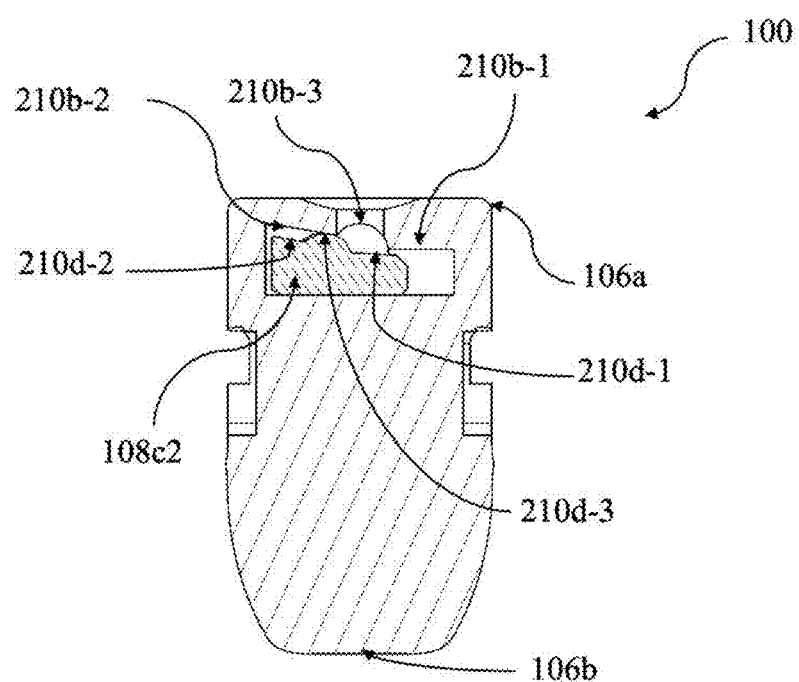

FIGS. 8a, 8b, 8c, 8e, and 8f represent the process of another embodiment of the bone anchor (100) being installed, with FIGS. 8a and 8b being the perspective views of the entire bone anchor (100) and FIGS. 8c, 8e, and 8f being the side views showing the engagement of the locking cap member (108) with the screw head (106). FIG. 8d illustrates the profiles of the locking cap member (018) and the screw head (106), correspondingly opposite to those illustrated in FIG. 8c.

Figure 9:
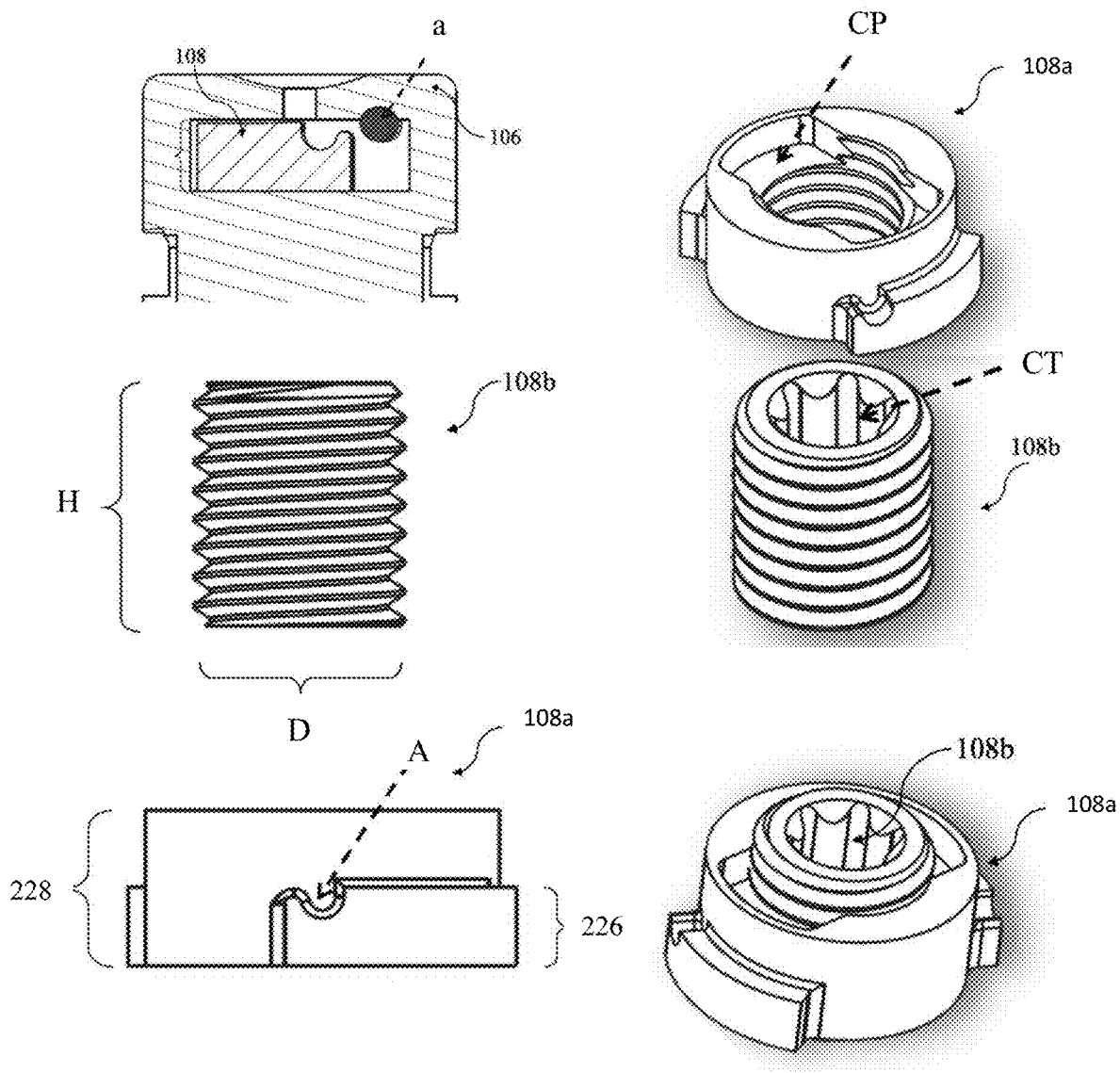

FIG. 9 illustrates the various parts of the components of one embodiment of the bone anchor (100) that are variable.

Figure 10:
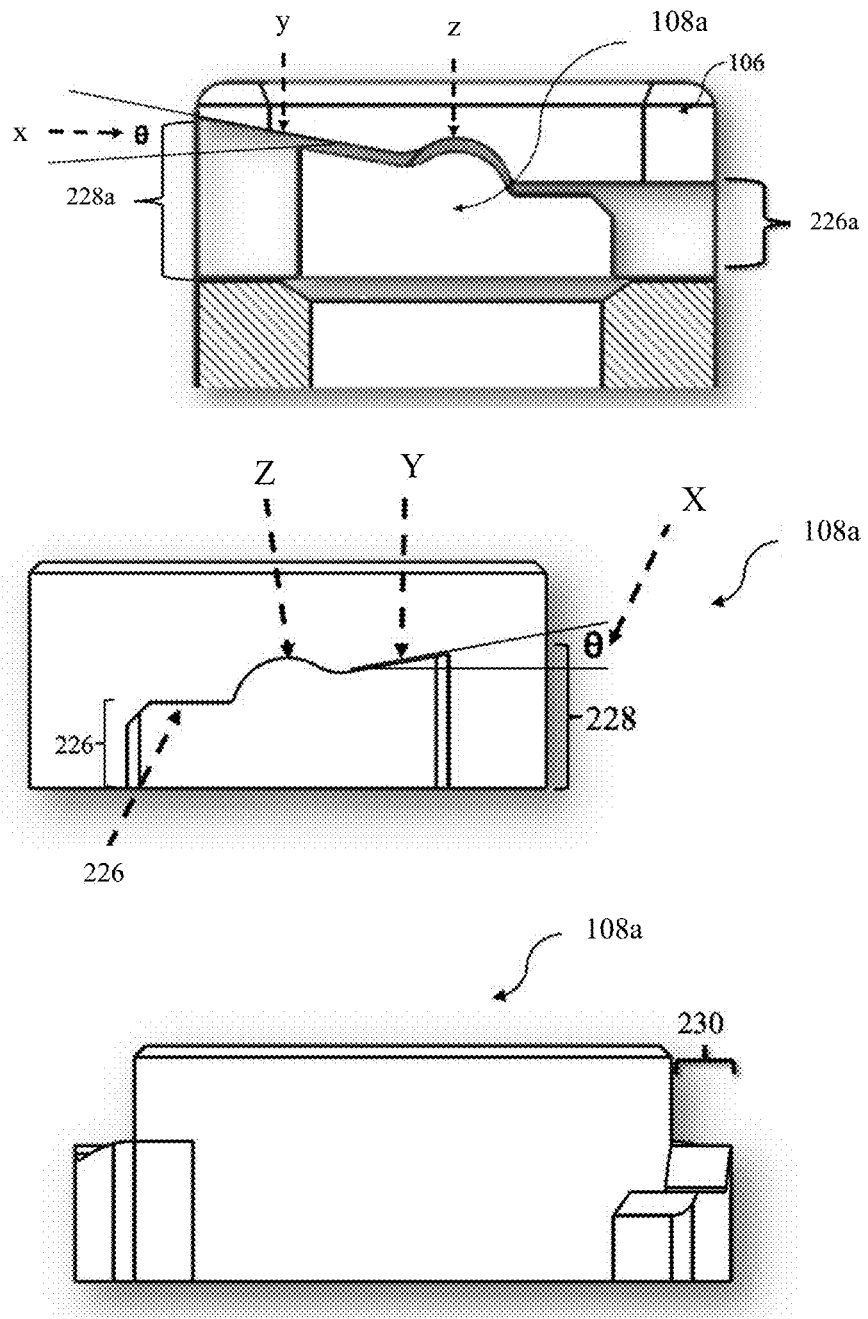

FIG. 10 illustrates the various parts of the components of another embodiment of the bone anchor (100) that are variable.

DESCRIPTION

The present disclosure provides an anti-splay bone anchor (100) for attaching at least one rod member (102) to a bone. As described in FIGS. 1a and 1b, the bone anchor (100) comprises a screw shank (104), a screw head (106) and a locking cap member (108) as the primary components. The characteristic design, shape and configuration of the screw head (106) and the locking cap member (108) and the consequent engagement mechanism there between, differentiates the bone anchor (100) of the present disclosure from those of the prior art and confers upon the present bone anchor (100), its technical advantages detailed herein below.

The screw shank (104) of the present disclosure is configured to affix the bone anchor (100) to the bone.

The screw head (106), as the name suggests, is the top portion of the screw shank (104) that is configured to receive the rod member (102), which is subsequently held in place by the locking cap member (108). The rod member, for the purpose of the present disclosure, is to be interpreted to include rods, plates and other elements commonly used in orthopaedic surgeries to affix to the bone. As illustrated in FIGS. 2a, 2b, 2c, 2d, 3a, 3b, and 3c, the screw head (106) of the present disclosure is characterized by having an operative first portion (106a), an operative second portion (106b) and at least one U-shaped conduit (106c) which is configured to receive the rod member (102) therein. The U-shaped conduit (106c) is defined by a first opposing member (106d1) having a first profile (110a, 210a) on its operative inner surface and a second opposing member (106d2) having a second profile (110b, 210b) on its operative inner surface. Together, the first opposing member (106d1) and the second opposing member (106d2) define an open operative upper end (106e1) and a closed operative lower end (106e2). A through hole (106f) is configured at and around the closed operative lower end (106e2) which is configured to receive the screw shank (104) there-through.

As described in FIGS. 4a, 4b, 4c, 5a, 5b, 5c, 6a, 6b, 6c and 6d the locking cap member (108) comprises a body (108a), a through hole (108h), a set screw (108b) and a first (108c1) and a second tab (108c2). The through hole (108h) is configured on the body (108a) and has threads configured on its operative inner surface. The set screw (108b) has threads configured on its outer surface and is threadably received in the through hole (108h). Further, the set screw (108b) is configured to abut and clamp the rod member (102) to the screw head (106). The first tab (108c1) and the second tab (108c2), each extend radially outward from an outer surface of the locking cap member (108) and have a third profile (110c, 210c) and a fourth profile (110d, 210d), respectively (illustrated in FIGS. 4b and 4c, and 5b and 5c, respectively).

It is an important feature of the bone anchor (100) of the present disclosure that the third profile (110c, 210c) and the fourth profile (110d, 210d) are complimentary to the first profile (110a, 210a) and the second profile (110b, 210b), respectively to facilitate an engagement (illustrated in FIGS. 7c, 7d, 7e, 7f, 8c, 8d, 8e, and 8f).

In an operative configuration, after the receipt of the rod member (102) within the screw head (106), the locking cap member (108) is received in the U-shaped conduit (106c) of the screw head (106) (illustrated in FIGS. 7a and 8a) and rotated therein through a predetermined angle, such that a clearance is maintained there-between (illustrated in FIGS. 7b and 8b). The predetermined angle ranges from 10 degrees to 150 degrees. In one embodiment, the predetermined angle is 90 degrees. After completing the rotation of the locking cap member (108), an interference is experienced between the first tab (108c1) and the second tab (108c2) with the first profile (110a, 210a) and the second profile (110b, 210b), respectively (illustrated in FIGS. 7c, 7d, 8c, and 8d). The interference is axial and is designed to be overcome by manually rotating the locking cap member (108) further until no rotation is possible (illustrated in FIGS. 7e and 8e). Thereafter, post the receipt and tightening of the set screw (108b) the through hole (108h), the locking cap member (108) is lifted up to facilitate the engagement of the first (110a, 210a) and the second profile (110b, 210b) with the third (110c, 210c) and the fourth profile (110d, 210d) respectively; thereby causing the locking cap member (108) to be positively locked in the axial direction (illustrated in FIGS. 7f and 8f).

Figure 2A:
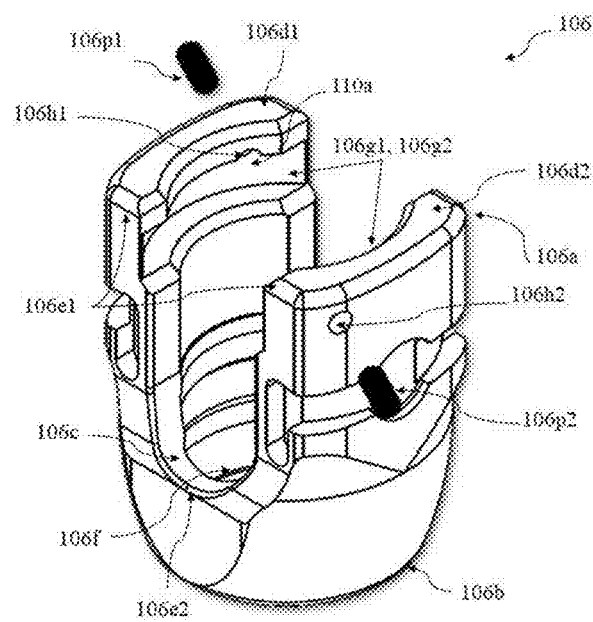
FIG. 2a illustrates a perspective view of one embodiment of the screw head (106) with the unsecured first and second pins (106p1, 106p2).
Figure 2B:
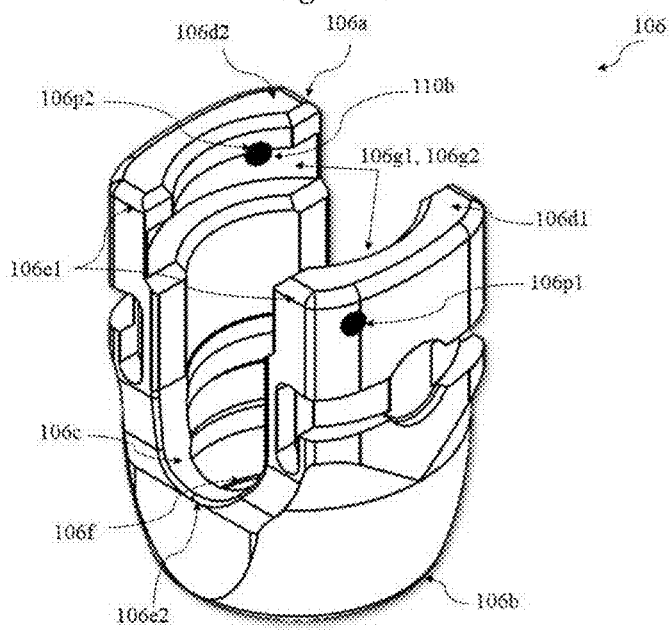
FIG. 2b illustrates a perspective view of one embodiment of the screw head (106) with the first and second pins (106p1, 106p2) secured in the first and second through holes, respectively (106h1, 106h2).
Figure 2C:
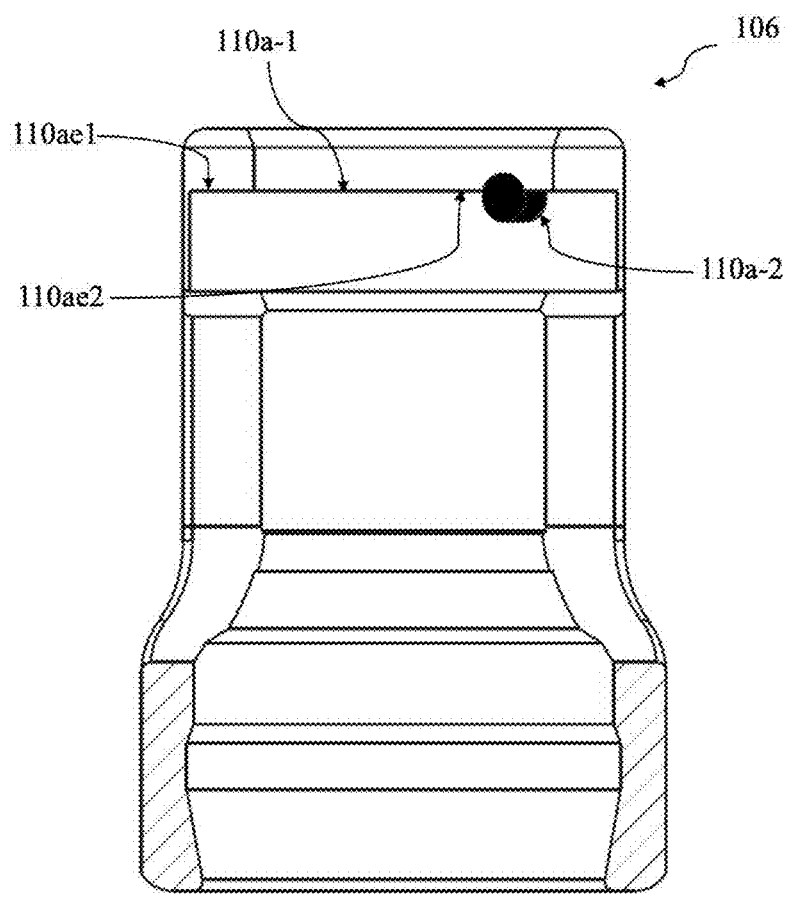
FIGS. 2c and 2d illustrate sectional side views of one embodiment of the screw head (106) for enhanced clarity on the first profile (110a) and the second profile (110b), respectively.
Figure 2D:
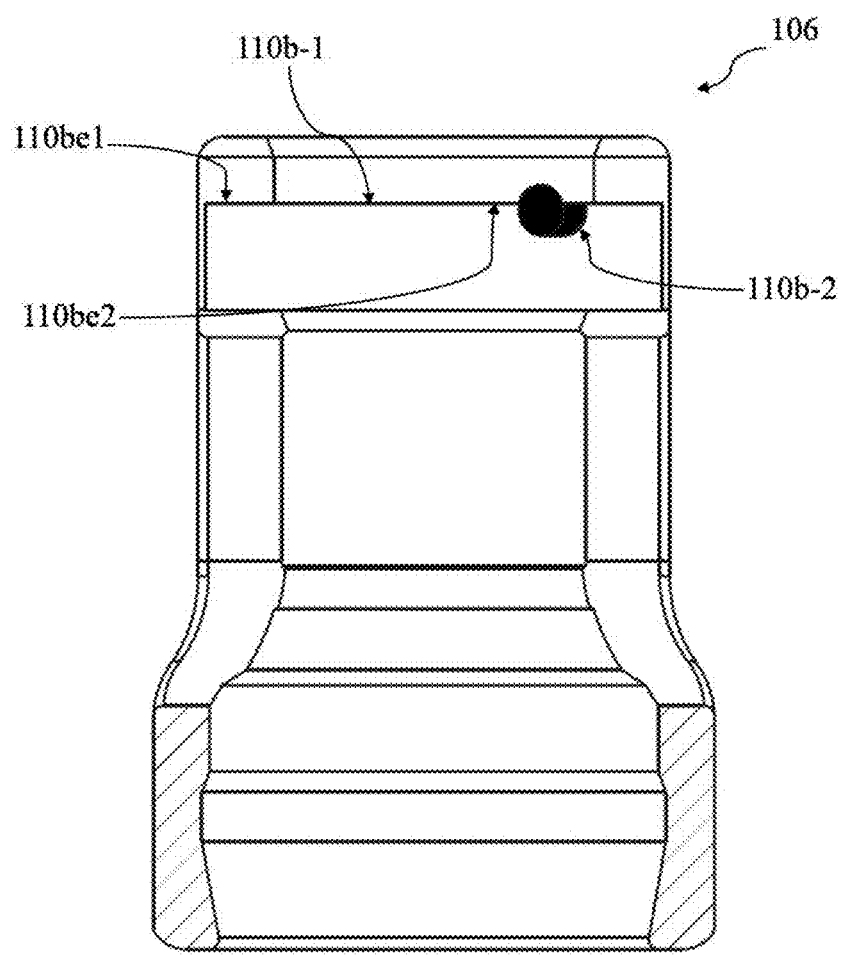

In one embodiment, the first profile (110a) and the second profile (110b) of the screw head (106) are characterized by having the configuration described herein after (illustrated in FIGS. 2a, 2b and particularly, 2c and 2d). The first opposing member (106d1) and the second opposing member (106d2) of the screw head (106) has a first radial slot (106g1) and a second radial slot (106g2) configured on its inner surface, respectively. The first radial slot (106g1) and the second radial slot (106g2) is configured to receive the first tab (108c1), and the second tab (108c2), of the locking cap member (108) respectively. A first through hole (106h1) and a second through hole (106h2) are configured on the first opposing member (106d1) and the second opposing member (106d2), respectively, such that a portion of both the holes, falls in the first radial slot (106g1) and the second radial slot (106g2) respectively and another portion is adjacent to the radial slots (106g1, 106g2). A first pin (106p1) and a second pin (106p2) is configured to be securely received in the first through hole (106h1) and the second through hole (106h2), respectively. The first pin (106p1) and the second pin (106p2) is secured by at least one method selected from the group consisting of welding, threading, press-fitting, glue, and any combinations thereof. In view of the above, as illustrated in FIGS. 2c and 2d, the first profile (110a), shown in FIG. 2c, and the second profile (110b), shown in FIG. 2d, are defined by a substantially flat portion (110a-1, 110-b1) having a proximal end (110ae1, 110be1) and a distal end (110*ae*2, 110*be*2) and a trough (110*a*-2, 110*b*-2) extending from the distal end (110*ae*2, 110*be*2) of the flat portion (110*a*-1, 110*b*-1).

Figure 4A:
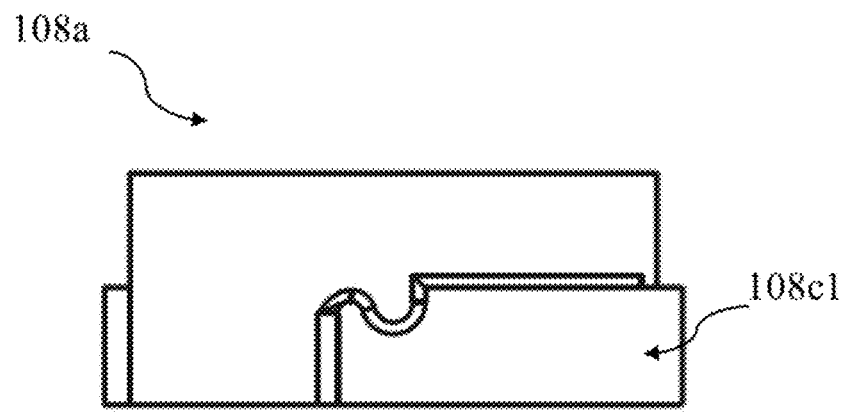
FIG. 4a is a side view of one embodiment of the locking cap member (108).
Figure 4B:
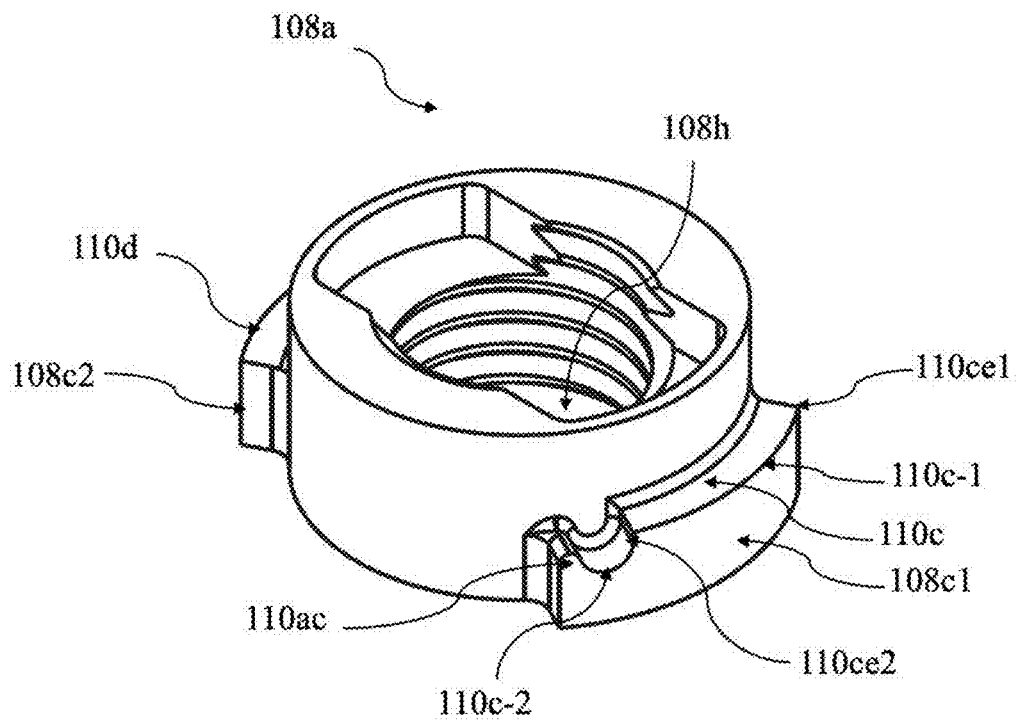
FIGS. 4b and 4c illustrate perspective views of one embodiment of the locking cap member (108) for enhanced clarity of the third profile (110c) and the fourth profile (110d), respectively.
Figure 4C:
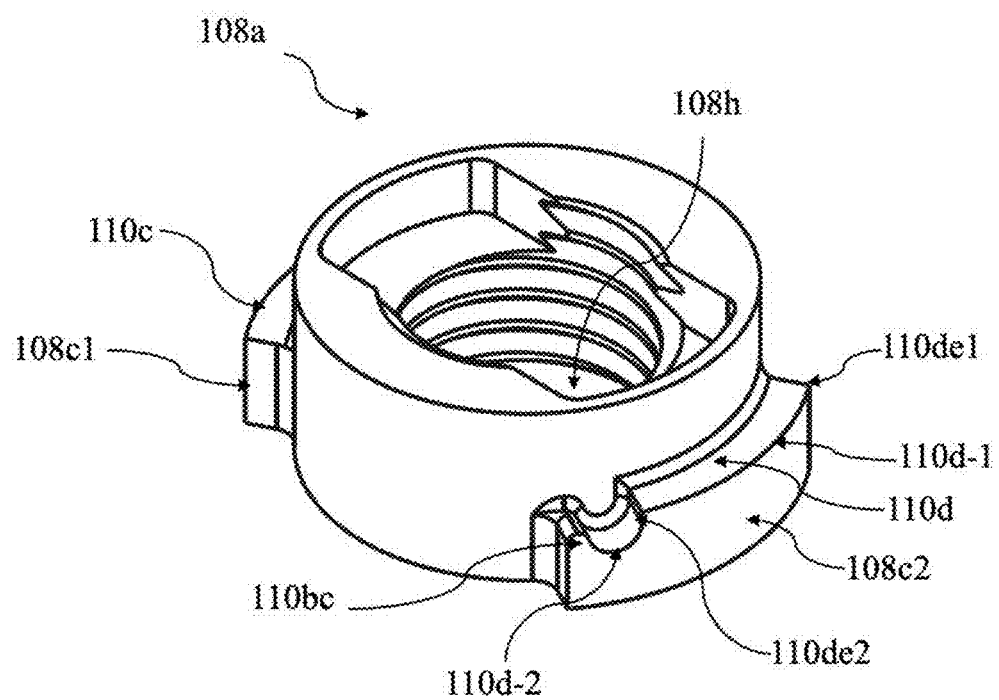

In the same embodiment, the third profile (110*c*), shown in FIG. 4*b*, and the fourth profile (110*d*), shown in FIG. 4*c*, of the locking cap member (108) are characterized by having the configuration described herein after (illustrated in FIG. 4*a* and particularly 4*b* and 4*c*). The third profile (110*c*) and the fourth profile (110*d*) is defined by a substantially flat portion (110*c*-1, 110*d*-1) having a proximal end (110*ce*1, 110*de*1) and a distal end (110*ce*2, 110*de*2), a trough (110*c*-2, 110*d*-2) extending from the distal end (110*ce*2, 110*de*2) of the flat portion (110*c*-1, 110*d*-1) and a crest (110*ac*, 110*bc*) adjacent to the trough (110*c*-2, 110*d*-2).

It is a characteristic of the configuration of the present screw head (106) and the locking cap member (108) that the trough (110*c*-2, 110*d*-2) on the third (110*c*) and fourth profile (110*d*) of the locking cap member (108) is complimentary to the trough (110*a*-2, 110*b*-2) on the first profile (110*a*) and second profile (110*b*) of the screw head (106). Furthermore, the trough (110*a*-2, 110*b*-2) on the first (100*a*) and second profile (110*b*) is configured to receive the trough (110*c*-2, 110*d*-2) on the third (110*c*) and fourth profile (110*d*), after overcoming the interference between the trough (110*a*-2, 110*b*-2) and the crest (110*ac*, 110*bc*), as illustrated in FIGS. 7*c*, 7*e*, and 7*f*.

Figure 3A:
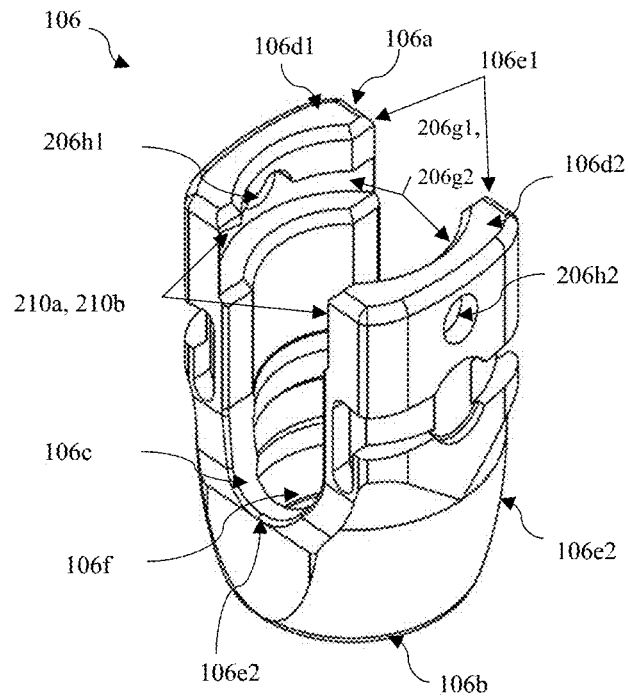
FIG. 3a illustrates a perspective view of another embodiment of the screw head (106).
Figure 3B:
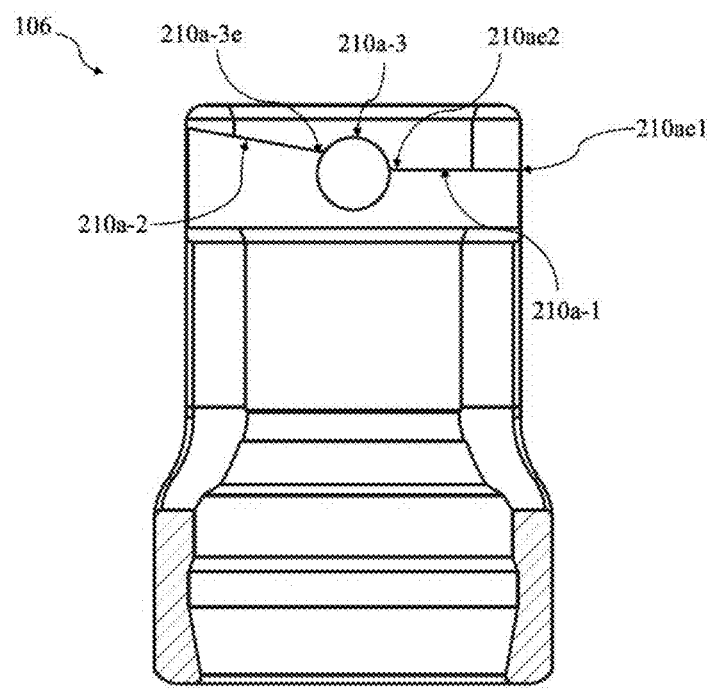
FIGS. 3b and 3c illustrate sectional side views of another embodiment of the screw head (106) for enhanced clarity of the first profile (210a) and the second profile (210b), respectively.
Figure 3C:
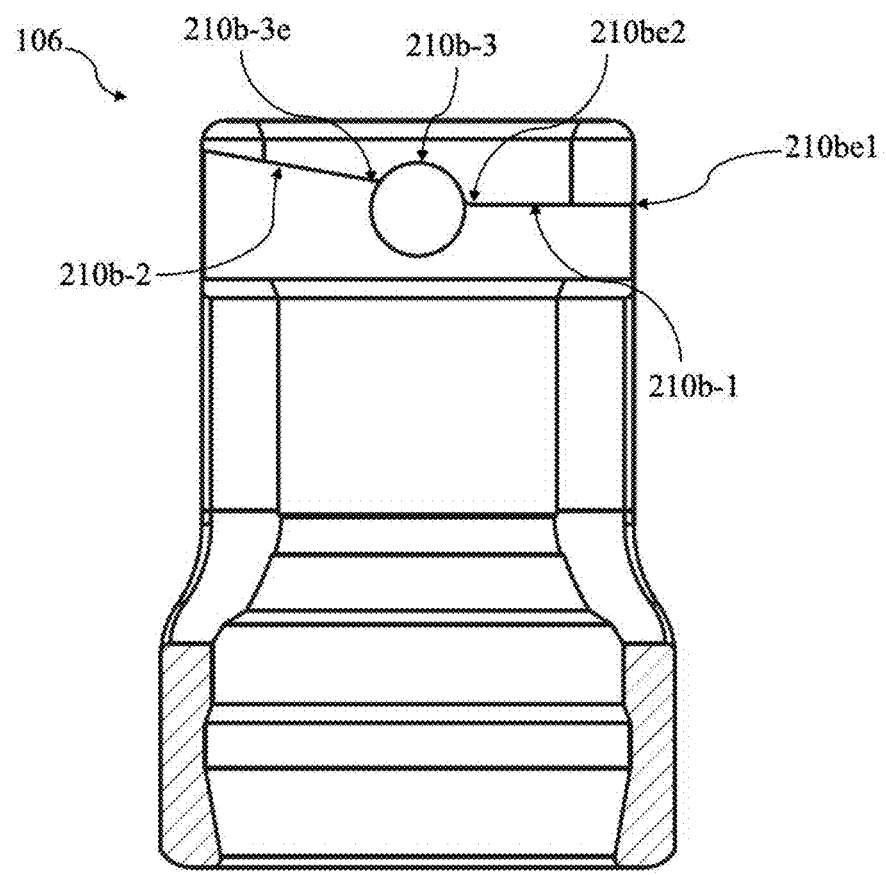

In another embodiment, the first profile (210*a*), and the second profile (210*b*) of the screw head (106) are characterized by having the configuration described herein after (as illustrated in FIGS. 3*a* and particularly, 3*b* and 3*c*). The first opposing member (106*d*1), shown in FIG. 3*b*, and the second opposing member (106*d*2), shown in FIG. 3*c*, of the screw head (106) have a first radial slot (206*g*1) and a second radial slot (206*g*2) configured on its inner surface, respectively. The first radial slot (206*g*1), and the second radial slot (206*g*2) are configured to receive the first tab (108*c*1), and the second tab (108*c*2) of the locking cap member (108), respectively. A third through hole (206*h*1) and a fourth through hole (206*h*2) are configured on the first opposing member (106*d*1) and the second opposing member (106*d*2), respectively. As illustrated in FIGS. 3*b* and 3*c*, in view of the above, the first profile (210*a*) and the second profile (210*b*) are defined by a substantially flat portion (210*a*-1, 210*b*-1) having a proximal end (210*ae*1, 210*be*1) and a distal end (210*ae*2, 210*be*2), a curvilinear portion (210*a*-3, 210*b*-3) extending from the distal end (210*ae*2, 210*be*2) of the flat portion (210*a*-1, 210*b*-1) and an inclined portion (210*a*-2, 210*b*-2) extending from an operative end (210*a*-3*e*, 210*b*-3*e*) of the curvilinear portion (210*a*-3, 210*b*-3). It is pertinent to note that the curvilinear portion (210*a*-3, 210*b*-3) is the upper circumference of the third through hole (206*h*1) and the fourth through hole (206*h*2), respectively.

Figure 5A:
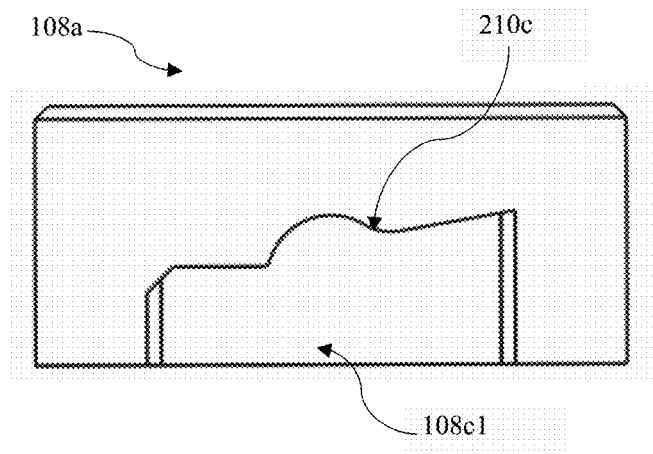
FIG. 5a illustrates a side view of another embodiment of the locking cap member (108).
Figure 5B:
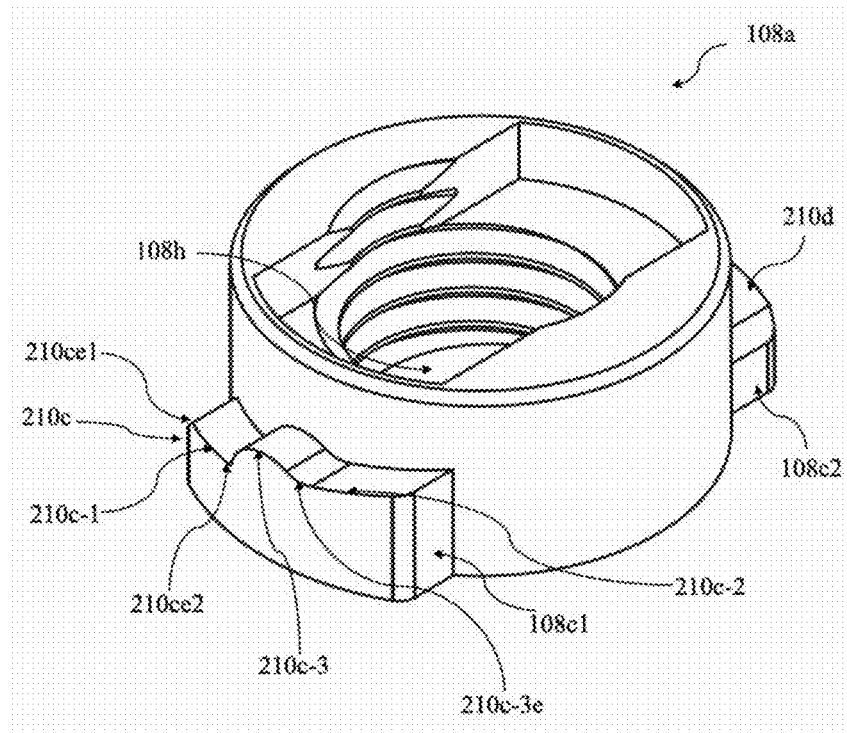
FIGS. 5b and 5c illustrate perspective views of another embodiment of the locking cap member (108) for enhanced clarity of both the third profile (210c) and the fourth profile (210d), respectively.
Figure 5C:
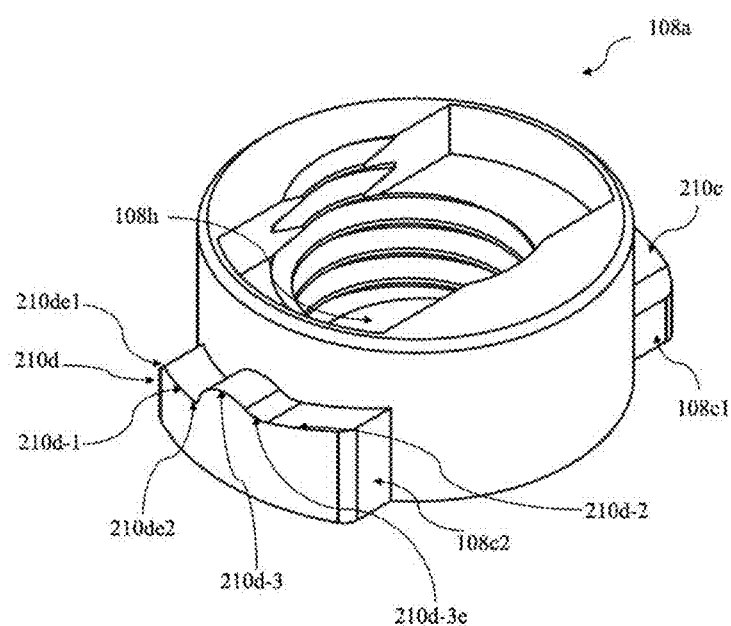
Figure 6A:
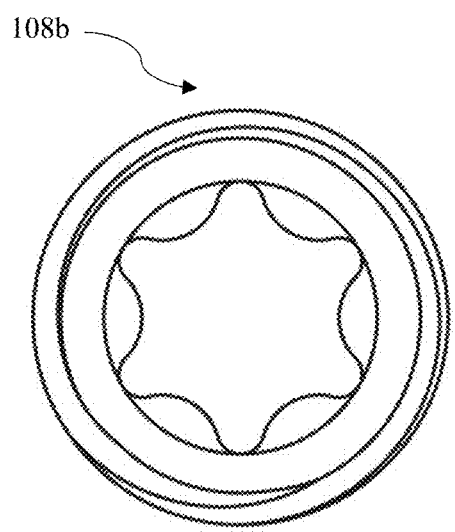
FIGS. 6a, 6b, 6c and 6d are the various views of the set screw (108b) component of the locking cap member (108).
Figure 6B:
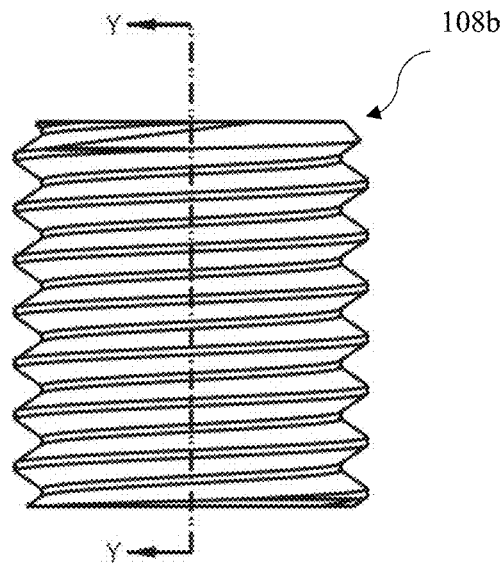
Figure 6C:
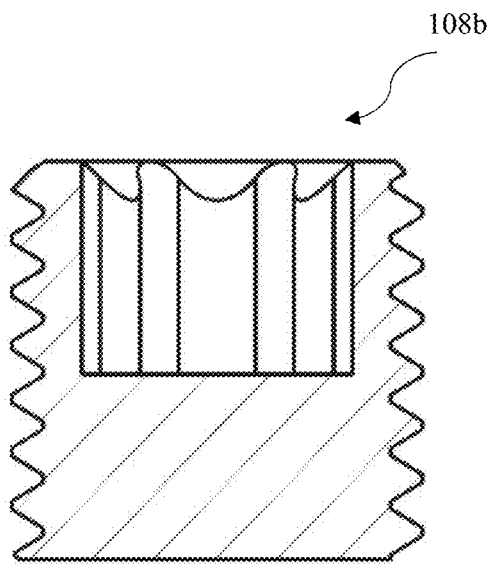
Figure 6D:
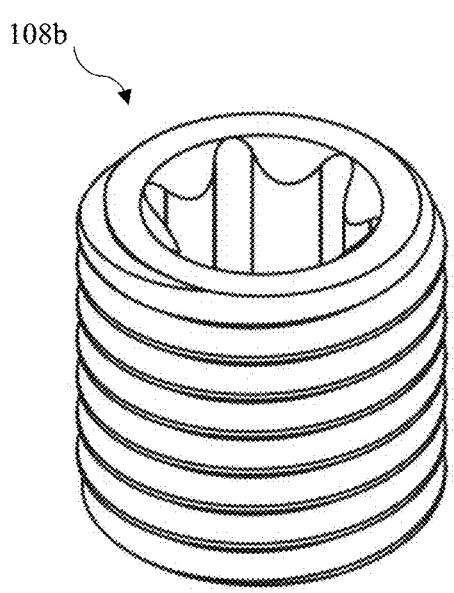

In the same embodiment, as illustrated in FIGS. 5*a* and particularly 5*b* and 5*c*, the third profile (210*c*), shown in FIG. 5*b*, and the fourth profile (210*d*), shown in FIG. 5*c*, of the locking cap member (108) are characterized by having the configuration described herein after. The third profile (210*c*) and the fourth profile (210*d*) are defined by a substantially flat portion (210*c*-1, 210*d*-1) having a proximal end (210*ce*1, 210*de*1) and a distal end (210*ce*2, 210*de*2) and a curvilinear portion (210*c*-3, 210*d*-3) extending from the distal end (210*ce*2, 210*de*2) of the flat portion (210*c*-1, 210*d*-1) and an inclined portion (210*c*-2, 210*d*-2) extending from the operative end (210*c*-3*e*, 210*d*-3*e*) of the curvilinear portion (210*c*-3, 210*d*-3) (illustrated in FIGS. 5*b* and 5*c*).

It is a characteristic of the configuration of the present screw head (106) and the locking cap member (108) that, the curvilinear portion (210*c*-3, 210*d*-3) on the third (110*c*) and fourth profile (110*d*) of the locking cap member (108) is complimentary to the curvilinear portion (210*a*-3, 210*b*-3) on the first (210*a*) and second (210*b*) profile of the screw head (106). Furthermore, the substantially flat portion (210*a*-1, 210*b*-1), curvilinear portion (210*a*-3, 210*b*-3) and inclined portion (210*a*-2, 210*b*-2) on the first (210*a*) and second (210*b*) profile are configured to receive the substantially flat portion (210*c*-1, 210*d*-1), curvilinear portion (210*c*-3, 210*d*-3) and inclined portion (210*c*-2, 210*d*-2) on the third (210*c*) and fourth profile (210*d*) after overcoming the interference between the curvilinear portion (210*c*-3, 210*d*-3) and the operative end (210*a*-3*e*, 210*b*-3*e*) of the curvilinear portion (210*a*-3, 210*b*-3), as illustrated in FIGS. 8*c*, 8*e*, and 8*f*.

The characteristic design, shape and configuration of the screw head (106) and the locking cap member (108) and the engagement mechanism there-between, as described herein above, confers upon the present bone anchor (100) the following crucial technical advantages.

Anti-Splay Due to Locking Cap (108) Being Non-Threaded

Since the locking cap (108) of the present bone anchor (100) does not have threading on the outer operative surface and consequently does not threadably engage with the screw head (106), splay of the screw head (106) is drastically reduced. An additional advantage of this feature is that the cap insertion becomes easy and does not lead to cross threading.

Anti-Splay Due to Axial Interference Between the Locking Cap (108) and Screw Head (106)

The locking mechanism in the existing bone anchor or pedicle screw systems of the prior art consists of circumferential interference between the locking cap and screw head. This causes the undue splaying of the screw head. In order to keep the construct intact, splaying should be minimal. Due to the characteristic design and configuration of the components of the present bone anchor (100), there is axial interference instead of circumferential or radial interference; thereby significantly reducing the amount of splay.

Further, since the tabs of the locking cap (108*c*1, 108*c*2) rotate and rest in the radial slots (106*g*1, 106*g*2, 206*g*1, 206*g*2) of the screw head (106) with a clearance therebetween; splay of the screw head (106) is further reduced.

Positive Locking Preventing Accidental Back Out of the Locking Cap (108)

Currently available bone anchor or pedicle screw systems do not have positive locking of the non-threaded cap to prevent accidental anti-clockwise rotation (rotational/linear). Locking of the non-threaded cap in the available systems is on the basis of friction. In the present bone anchor (100), there is positive locking of the locking cap (108) that is feature/profile based and not friction based.

Further, the currently available systems have an additional provision or stop to restrict the rotation of the locking cap past its desired final position. In the present bone anchor (100), the final position of the cap is ensured as a result of the profile and no additional feature or component is needed to restrict further rotation.

The inventors of the present disclosure after numerous iterations have arrived at the afore-stated bone anchor (100). The most challenging part has been the development of the shape of the radial slot, which is easy to manufacture, should prevent the accidental backing out of the cap in the absence of external actuation and should displace in the vertical direction to provide positive locking.

Different variations in the shape, configuration and dimensions of the bone anchor (100) of the present disclosure and its components are possible that give similar results. For one of the embodiments, as described in FIG. 9, in case of the screw head (106), changes in the dimensions of height and depth of the radial slot, diameter of the pin (a), location of the pin and/or shape of the pin will also give similar results. Instead of press fitted/laser welded external pin, a radial slot can be shaped/sized to make a similar pin type feature in the slot itself. In this case, no additional pins will be required and this pin type feature would be the integral feature of the slot. This will also give similar results. In case of the locking cap (108), changes in the connection type (CT), diameter (D) and height (H) of the set-screw (108b) will give similar results. Changes in the length and height (226) of the external tabs of the non-threaded cap, total height (228) of the cap and the size, shape and location of the trough (A) will give similar results. Change in the shape, size and location of the connection portion (CP) of the non-threaded cap will also give similar results (parts capable of showing variations demarcated by dotted line and/or curved bracket).

In one of the other embodiments, as indicated in FIG. 10, in case of the locking cap, changes in the dimensions of angle of the inclined portion (X), length of the inclined portion (Y), diameter of the curvilinear portion (Z), height of the horizontal portion of the tab (226), height of the tab (228) and/or width of the tab (230) will give similar results. Instead of semi circular portion, shape can also be oval, oblong or any other shape. The reversal of the orientation of the inclined portion and horizontal portion will give similar results. In case of screw head, changes in the dimensions of the angle of the inclined portion (x), length of the inclined portion (y), diameter of the semi-circular portion (z), height of the substantially flat portion (226a), height of the radial slot (228a) and/or width of the radial slot in the screw head (106) will result in the same locking mechanism. The reversal of the orientation of the inclined portion and horizontal portion will give similar results (parts capable of showing variations demarcated by dotted line and/or curved bracket).

The afore-stated components of the system (100) of the present disclosure are manufactured from biocompatible materials. Further, the components of the system (100) of the present disclosure are manufactured from at least one material selected from the group that includes but is not limited to metal(s), metal alloys and polymers. For the purpose of the present disclosure, the term metal is at least one selected from the group that includes but is not limited to titanium, cobalt-chromium-molybdenum, and stainless steel or any other metal or metal alloy suitable from biocompatibility and strength perspective. For the purpose of the present disclosure, the term polymers is at least one selected from the group that includes but is not limited to high density polyethylene (HDPE), polyurethane, polycarbonate urethane, ultra-high molecular weight polyethylene (UHMWPE), polyethylene terephthalate (PET), polyether ether ketone (PEEK) and silicone or any other polymer suitable from biocompatibility and strength perspective. All the components of the system (100) of the present disclosure may be fabricated separately and attached together using conventional manufacturing techniques.

TECHNICAL ADVANTAGES AND ECONOMIC SIGNIFICANCE

The technical advantages and economic significance of the anti-splay bone anchor (100) of the present disclosure are presented herein after:

Anti-splay
Ease of insertion of locking cap during surgery
Less time required for locking the rod member onto the screw head
Eliminates problems associated with cross-threading
Less number of components or sub-parts
Economical
Made from biocompatible materials

We claim:

1. An anti-splay bone anchor for attaching at least one rod member to a bone, said bone anchor comprising:
   (a) a screw shank for affixing said bone anchor to said bone;
   (b) a screw head having:
      I. an operative first portion and an operative second portion;
      II. at least one U-shaped conduit being configured to receive said rod member therein, said at least one U-shaped conduit defined by:
         i. a first opposing member having a first profile defined on an operative inner surface thereof; and
         ii. a second opposing member having a second profile defined on an operative inner surface thereof;
         said first opposing member, and said second opposing member defining an open operative upper end, and a closed operative lower end;
         iii. a through hole being configured at and around said closed operative lower end, said through hole being configured to receive said screw shank there-through; and
   (c) a locking cap member having:
      I. a body;
      II. a through hole configured on said body, said through hole having threads configured on an operative inner surface thereof;
      III. a set screw having threads configured on an outer surface thereof, said set screw:
         i. being threadably received in said through hole; and
         ii. configured to abut and clamp said rod member to said screw head; and
      IV. a first tab and a second tab:
         i. each extending radially outward from an outer surface of said locking cap member; and
         ii. having a third profile, and a fourth profile, respectively, said third profile, and said fourth profile being complimentary to said first profile and said second profile, respectively;
      wherein in an operative configuration,
      after receipt of said rod member within said at least one U-shaped conduit, said locking cap member is adapted to be received in said open operative upper end and rotated through a predetermined angle, such that a clearance is maintained in between said locking cap member and said first opposing member and said second opposing member;
      wherein after completing the rotation of said locking cap member through said predetermined angle, there is an interference between said first tab, and said second tab with said first profile and said second profile, respectively; said interference being axial and designed to be overcome by rotating said locking cap member further until no rotation is possible; and
      after receipt and tightening of said set screw in said through hole, said locking cap member is lifted up to facilitate the engagement of said first profile, and said second profile with said third profile, and said fourth profile, respectively; thereby causing said locking cap member to be positively locked in the axial direction.

2. The anti-splay bone anchor as claimed in claim 1, wherein:
(a) each of said first profile and said second profile having:
   I. a first radial slot and a second radial slot configured on an inner surface of said first opposing member and said second opposing member, respectively, said first radial slot and second radial slot being configured to receive said first tab and said second tab, respectively;
   II. a first through hole and a second through hole being configured on said first opposing member and said second opposing member, respectively, such that:
      i. a portion of said first through hole and said second through hole being configured on said first opposing member and second opposing member, adjacent to said first radial slot, and said second radial slot; and
      ii. another portion of said first through hole and said second through hole being configured on said first radial slot and said second radial slot;
   III. a first pin and a second pin configured to be securely received in said first through hole and said second through hole, respectively;
      wherein said first profile and said second profile defining:
         i. a substantially flat portion, having a proximal end and a distal end; and
         ii. a trough extending from said distal end of said flat portion; and
(b) each of said third profile and said fourth profile having:
   I. a substantially flat portion having a proximal end and a distal end; and
   II. a trough extending from said distal end of said flat portion, said trough being complimentary to a trough of said first profile and second profile;
   III. a crest adjacent to said trough,
      wherein said trough is configured to receive said trough, after overcoming the interference between said trough and said crest.

3. The anti-splay bone anchor as claimed in claim 2, wherein each of said first pin and said second pin being secured by at least one method selected from the group consisting of welding, threading, press-fitting, glue, and any combinations thereof.

4. The anti-splay bone anchor as claimed in claim 1, wherein
(a) each of said first profile and said second profile having:
   I. a first radial slot and a second radial slot configured on an inner surface of said first opposing member and said second opposing member, respectively, said first radial slot and said second radial slot being configured to receive said first tab and said second tab, respectively;
   II. a third through hole and a fourth through hole being configured on said first opposing member and said second opposing member, respectively,
      wherein said first profile and said second profile defining
         i. a substantially flat portion having a proximal end and a distal end;
         ii. a curvilinear portion extending from said distal end of said flat portion; and
         iii. an inclined portion extending from an operative end of said curvilinear portion;
      wherein the curvilinear portion being the upper circumference of the third through hole and the fourth through hole, respectively,
(b) each of said third profile and said fourth profile having:
   I. a substantially flat portion having a proximal end and a distal end; and
   II. a curvilinear portion extending from said distal end of said flat portion, said curvilinear portion being complementary to said curvilinear portion; and
   III. an inclined portion extending from an operative end of said curvilinear portion;
      said substantially flat portion, curvilinear portion and inclined portion receive said substantially flat portion, curvilinear portion and inclined portion after overcoming the interference between said curvilinear portion and said operative end of said curvilinear portion.

5. The anti-splay bone anchor as claimed in claim 1, being made from one or more biocompatible materials.

6. The anti-splay bone anchor as claimed in claim 1, wherein said predetermined angle is in the range of 10 degrees to 150 degrees.

* * * * *